US011166837B2

(12) United States Patent
Lesko et al.

(10) Patent No.: US 11,166,837 B2
(45) Date of Patent: *Nov. 9, 2021

(54) OSTOMY POUCH WITH FILTERING SYSTEM

(71) Applicant: ConvaTec Technologies Inc., Las Vegas, NV (US)

(72) Inventors: Marc Lesko, Jackson, NJ (US); Mingliang Lawrence Tsai, Holmdel, NJ (US); Gary Oberholtzer, Feasterville, PA (US)

(73) Assignee: ConvaTec Technologies Inc., Las Vegas, NV (US)

( * ) Notice: Subject to any disclaimer, the term of this patent is extended or adjusted under 35 U.S.C. 154(b) by 355 days.

This patent is subject to a terminal disclaimer.

(21) Appl. No.: 16/272,673

(22) Filed: Feb. 11, 2019

(65) Prior Publication Data

US 2019/0247220 A1 Aug. 15, 2019

Related U.S. Application Data

(63) Continuation of application No. 13/248,704, filed on Sep. 29, 2011, now Pat. No. 10,285,847.

(60) Provisional application No. 61/388,331, filed on Sep. 30, 2010.

(51) Int. Cl.
| *A61F 5/441* | (2006.01) |
| *A61F 5/445* | (2006.01) |
| *A61F 5/448* | (2006.01) |
| *A61F 5/44* | (2006.01) |

(52) U.S. Cl.
CPC ............ *A61F 5/441* (2013.01); *A61F 5/4405* (2013.01); *A61F 5/445* (2013.01); *A61F 5/448* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,074,851 A * | 12/1991 | Plass | ................... | A61F 5/441 604/333 |
| 5,250,042 A * | 10/1993 | Torgalkar | ............... | A61F 5/441 604/333 |
| 5,306,264 A * | 4/1994 | Ferguson | ............... | A61F 5/441 604/333 |
| 5,401,264 A * | 3/1995 | Leise, Jr. | ............... | A61F 5/441 604/333 |
| 5,643,234 A * | 7/1997 | Lesko | ................... | A61F 5/441 604/333 |
| 7,083,569 B2 * | 8/2006 | Boulanger | ............ | A61F 5/445 600/32 |

(Continued)

FOREIGN PATENT DOCUMENTS

| GB | 2534012 A | 7/2016 |
| GB | 2544180 A | 5/2017 |

(Continued)

OTHER PUBLICATIONS

US 10,806,622 B2, 10/2020, Hansen et al. (withdrawn)

*Primary Examiner* — Guy K Townsend
(74) *Attorney, Agent, or Firm* — Taft Stettinius & Hollister LLP; Ryan O. White; Derek B. Lavender

(57) ABSTRACT

An ostomy appliance including an ostomy pouch with a filter and a center pleated panel to protect the filter, facilitate deodorization and deter ballooning.

10 Claims, 5 Drawing Sheets

(56) References Cited

U.S. PATENT DOCUMENTS

| | | | |
|---|---|---|---|
| 7,214,217 B2* | 5/2007 | Pedersen | A61F 5/441 604/332 |
| 7,476,220 B2* | 1/2009 | Lillegaard | A61F 5/4404 4/144.2 |
| 7,572,492 B2* | 8/2009 | Bager | B29C 66/532 428/35.2 |
| 7,604,622 B2* | 10/2009 | Pedersen | A61F 5/448 604/333 |
| 8,449,513 B2 | 5/2013 | Abrams | |
| 8,979,811 B2 | 3/2015 | Keleny et al. | |
| 9,968,480 B2 | 5/2018 | Nyberg | |
| 10,278,857 B2 | 5/2019 | Hansen et al. | |
| 10,285,847 B2* | 5/2019 | Lesko | A61F 5/441 604/333 |
| D862,691 S | 10/2019 | Fenton | |
| 10,434,015 B2 | 10/2019 | Taylor et al. | |
| 10,434,309 B2 | 10/2019 | Forsell | |
| 10,449,081 B2 | 10/2019 | Lee | |
| 10,449,082 B2 | 10/2019 | Johnsen | |
| 10,463,527 B2 | 11/2019 | Gallant et al. | |
| 10,470,917 B2 | 11/2019 | Chang | |
| 10,470,918 B2 | 11/2019 | Bendix | |
| 10,471,173 B2 | 11/2019 | Misawa | |
| 10,478,328 B2 | 11/2019 | Guidry et al. | |
| 10,478,329 B2 | 11/2019 | Oberholtzer et al. | |
| 10,478,330 B2 | 11/2019 | Wiltshire et al. | |
| 10,500,084 B2 | 12/2019 | Hansen et al. | |
| 10,500,315 B2 | 12/2019 | Chang et al. | |
| 10,507,318 B2 | 12/2019 | Jin et al. | |
| 10,512,562 B2 | 12/2019 | Kavanagh et al. | |
| 10,524,953 B2 | 1/2020 | Hanuka et al. | |
| 10,531,978 B2 | 1/2020 | Haas et al. | |
| 10,537,461 B2 | 1/2020 | Hanuka et al. | |
| 10,537,462 B1 | 1/2020 | Hatchett et al. | |
| 10,583,029 B2 | 3/2020 | Chang | |
| 10,588,773 B2 | 3/2020 | Tsai et al. | |
| 10,610,402 B1 | 4/2020 | Idowu et al. | |
| 10,617,554 B2 | 4/2020 | Luce | |
| 10,617,555 B2 | 4/2020 | James et al. | |
| 10,646,370 B2 | 5/2020 | Keleny et al. | |
| 10,653,551 B2 | 5/2020 | Apolinario et al. | |
| 10,660,784 B2 | 5/2020 | Nishtala et al. | |
| 10,660,785 B2 | 5/2020 | Kaufman et al. | |
| 10,660,786 B2 | 5/2020 | Obst et al. | |
| 10,729,806 B2 | 8/2020 | Bingol et al. | |
| 10,736,769 B2 | 8/2020 | Grove Sund et al. | |
| 10,744,224 B2 | 8/2020 | Israelson et al. | |
| 10,758,398 B2 | 9/2020 | Murthy Aravalli et al. | |
| 10,779,986 B2 | 9/2020 | Cox | |
| 10,799,385 B2 | 10/2020 | Hansen et al. | |
| 10,813,786 B2 | 10/2020 | Lysgaard | |
| 10,813,787 B2 | 10/2020 | Dinakara et al. | |
| 2003/0014023 A1* | 1/2003 | Kanbara | A61F 5/441 604/333 |
| 2003/0040727 A1* | 2/2003 | Boulanger | A61F 5/445 604/332 |
| 2004/0267216 A1 | 12/2004 | Udayakumar et al. | |
| 2005/0143696 A1* | 6/2005 | Pedersen | A61F 5/441 604/332 |
| 2006/0058576 A1 | 3/2006 | Davies et al. | |
| 2007/0049880 A1* | 3/2007 | Suehr | A61F 5/441 604/333 |
| 2007/0203466 A1* | 8/2007 | Pedersen | A61F 5/441 604/333 |
| 2008/0004580 A1* | 1/2008 | Mullejans | A61F 5/448 604/344 |
| 2009/0227973 A1* | 9/2009 | Worsoee | A61F 5/441 604/333 |
| 2009/0247970 A1* | 10/2009 | Keleny | B01D 46/0036 604/333 |
| 2010/0174253 A1 | 7/2010 | Cline et al. | |
| 2010/0241092 A1* | 9/2010 | Nguyen-Demary | A61P 31/00 604/336 |
| 2011/0218507 A1 | 9/2011 | Andersen et al. | |
| 2012/0041400 A1 | 2/2012 | Christensen | |
| 2012/0109086 A1 | 5/2012 | Tsai | |
| 2012/0136324 A1 | 5/2012 | Hanuka et al. | |
| 2012/0179124 A1 | 7/2012 | Nguyen-Demary et al. | |
| 2012/0283678 A1* | 11/2012 | Nguyen-Demary | A61F 5/441 604/337 |
| 2013/0072886 A1* | 3/2013 | Schertiger | A61F 5/445 604/333 |
| 2013/0085463 A1* | 4/2013 | Lesko | A61F 5/441 604/333 |
| 2013/0226063 A1 | 8/2013 | Taylor et al. | |
| 2014/0207094 A1 | 7/2014 | Chang | |
| 2014/0221950 A1 | 8/2014 | Chang et al. | |
| 2014/0288517 A1 | 9/2014 | Tsai et al. | |
| 2014/0316360 A1 | 10/2014 | Ekfeldt et al. | |
| 2015/0133881 A1 | 5/2015 | Freiding | |
| 2015/0209172 A1 | 7/2015 | Richmann et al. | |
| 2016/0151198 A1 | 6/2016 | Frampton et al. | |
| 2016/0193003 A1 | 7/2016 | Todd et al. | |
| 2016/0206469 A1 | 7/2016 | Prezelin | |
| 2017/0007440 A1 | 1/2017 | Moavenian | |
| 2017/0065451 A1 | 3/2017 | Brandt et al. | |
| 2017/0209295 A1 | 7/2017 | Smith et al. | |
| 2017/0209296 A1 | 7/2017 | Cailleteau | |
| 2018/0064572 A1 | 3/2018 | Wiltshire | |
| 2018/0235801 A1 | 8/2018 | Oellgaard et al. | |
| 2018/0236207 A1 | 8/2018 | Shankarsetty | |
| 2018/0303655 A1 | 10/2018 | Glithero et al. | |
| 2018/0311066 A1 | 11/2018 | Hansen et al. | |
| 2018/0344506 A1 | 12/2018 | Larsen | |
| 2018/0360644 A1 | 12/2018 | Alvarez Ponce | |
| 2018/0369474 A1 | 12/2018 | Falleboe et al. | |
| 2019/0015241 A1 | 1/2019 | Lin et al. | |
| 2019/0029868 A1 | 1/2019 | Grum-Schwensen et al. | |
| 2019/0110919 A1 | 4/2019 | Beckers et al. | |
| 2019/0117824 A1 | 4/2019 | Hansen et al. | |
| 2019/0247549 A1 | 8/2019 | Nielsen | |
| 2019/0321213 A1 | 10/2019 | Morrison, Sr. | |
| 2019/0328571 A1 | 10/2019 | Adachi | |
| 2019/0328572 A1 | 10/2019 | Weinberg et al. | |
| 2019/0358076 A1 | 11/2019 | Blatt | |
| 2019/0365560 A1 | 12/2019 | Timms et al. | |
| 2019/0374372 A1 | 12/2019 | Seres et al. | |
| 2019/0380860 A1 | 12/2019 | Eggert et al. | |
| 2019/0380861 A1 | 12/2019 | Nordquist et al. | |
| 2019/0380882 A1 | 12/2019 | Taylor et al. | |
| 2020/0000624 A1 | 1/2020 | Gibbons et al. | |
| 2020/0015996 A1 | 1/2020 | Schertiger | |
| 2020/0030134 A1 | 1/2020 | Hopper | |
| 2020/0038226 A1 | 2/2020 | Botten et al. | |
| 2020/0038227 A1 | 2/2020 | Makar, Jr. | |
| 2020/0038228 A1 | 2/2020 | Aravalli et al. | |
| 2020/0038229 A1 | 2/2020 | Aravalli | |
| 2020/0046541 A1 | 2/2020 | Sund et al. | |
| 2020/0046542 A1 | 2/2020 | Guidry et al. | |
| 2020/0046543 A1 | 2/2020 | Scalise et al. | |
| 2020/0054476 A1 | 2/2020 | Miller | |
| 2020/0054478 A1 | 2/2020 | Forsell | |
| 2020/0060863 A1 | 2/2020 | Sund et al. | |
| 2020/0061282 A1 | 2/2020 | Hvid et al. | |
| 2020/0069455 A1 | 3/2020 | Oberholtzer et al. | |
| 2020/0069529 A1 | 3/2020 | Starnes et al. | |
| 2020/0078206 A1 | 3/2020 | Chiladakis | |
| 2020/0085608 A1 | 3/2020 | Hrushka et al. | |
| 2020/0093633 A1 | 3/2020 | Blumrosen et al. | |
| 2020/0100931 A1 | 4/2020 | Schoess et al. | |
| 2020/0100946 A1 | 4/2020 | Wohlgemuth et al. | |
| 2020/0121490 A1 | 4/2020 | Woodward et al. | |
| 2020/0138618 A1 | 5/2020 | Roszkowiak et al. | |
| 2020/0138619 A1 | 5/2020 | Cisko, Jr. et al. | |
| 2020/0146944 A1 | 5/2020 | Moulton et al. | |
| 2020/0155338 A1 | 5/2020 | Meteer | |
| 2020/0163792 A1 | 5/2020 | Schertiger | |
| 2020/0164196 A1 | 5/2020 | Jin et al. | |
| 2020/0188160 A1 | 6/2020 | Udayakumar | |
| 2020/0188161 A1 | 6/2020 | Seres et al. | |
| 2020/0188162 A1 | 6/2020 | Menifee | |
| 2020/0197213 A1 | 6/2020 | Frampton-Vallance et al. | |
| 2020/0214371 A1 | 7/2020 | Apelt | |

(56) References Cited

U.S. PATENT DOCUMENTS

| | | |
|---|---|---|
| 2020/0214872 A1 | 7/2020 | Tretheway et al. |
| 2020/0214873 A1 | 7/2020 | Tretheway et al. |
| 2020/0214875 A1 | 7/2020 | Tretheway et al. |
| 2020/0229962 A1 | 7/2020 | Torstensen et al. |
| 2020/0237550 A1 | 7/2020 | Hussey et al. |
| 2020/0246173 A1 | 8/2020 | Schertiger et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0246178 A1 | 8/2020 | O'Hamill et al. |
| 2020/0253777 A1 | 8/2020 | Jones |
| 2020/0261254 A1 | 8/2020 | Williams et al. |
| 2020/0276044 A1 | 9/2020 | Tretheway et al. |
| 2020/0276045 A1 | 9/2020 | Bendavit |
| 2020/0281758 A1 | 9/2020 | Tan |
| 2020/0281761 A1 | 9/2020 | Tretheway et al. |
| 2020/0289307 A1 | 9/2020 | Tretheway et al. |
| 2020/0289308 A1 | 9/2020 | Tretheway et al. |
| 2020/0297524 A1 | 9/2020 | Hunt et al. |
| 2020/0306073 A1 | 10/2020 | Olsen et al. |
| 2020/0306074 A1 | 10/2020 | Speiermann et al. |
| 2020/0330258 A1 | 10/2020 | Hansen et al. |
| 2020/0330259 A1 | 10/2020 | Sund et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0338230 A1 | 10/2020 | Israelson et al. |

FOREIGN PATENT DOCUMENTS

| | | |
|---|---|---|
| GB | 2548673 A | 9/2017 |
| GB | 2550936 A | 12/2017 |
| GB | 2570526 A | 7/2019 |
| WO | 2015110544 A1 | 7/2015 |
| WO | 2015138190 A1 | 9/2015 |
| WO | 2015148035 A1 | 10/2015 |
| WO | 2018188706 A1 | 10/2018 |
| WO | 2018188707 A1 | 10/2018 |
| WO | 2019058126 A1 | 3/2019 |
| WO | 2019058127 A1 | 3/2019 |
| WO | 2019091526 A1 | 5/2019 |
| WO | 2019091527 A1 | 5/2019 |
| WO | 2019091528 A1 | 5/2019 |
| WO | 2019091529 A1 | 5/2019 |
| WO | 2019091532 A1 | 5/2019 |
| WO | 2019099662 A1 | 5/2019 |
| WO | 2019120424 A1 | 6/2019 |
| WO | 2019120429 A1 | 6/2019 |
| WO | 2019120430 A1 | 6/2019 |
| WO | 2019120432 A1 | 6/2019 |
| WO | 2019120433 A1 | 6/2019 |
| WO | 2019120434 A1 | 6/2019 |
| WO | 2019120437 A1 | 6/2019 |
| WO | 2019120438 A1 | 6/2019 |
| WO | 2019120439 A1 | 6/2019 |
| WO | 2019120442 A1 | 6/2019 |
| WO | 2019120443 A1 | 6/2019 |
| WO | 2019120444 A1 | 6/2019 |
| WO | 2019120446 A1 | 6/2019 |
| WO | 2019120448 A1 | 6/2019 |
| WO | 2019120449 A1 | 6/2019 |
| WO | 2019120450 A1 | 6/2019 |
| WO | 2019120451 A1 | 6/2019 |
| WO | 2019120452 A1 | 6/2019 |
| WO | 2019120458 A1 | 6/2019 |
| WO | 2019197291 A1 | 10/2019 |
| WO | 2019197971 A1 | 10/2019 |
| WO | 2019198012 A1 | 10/2019 |
| WO | 2019221830 A1 | 11/2019 |
| WO | 2019229267 A2 | 12/2019 |
| WO | 2019229268 A1 | 12/2019 |
| WO | 2019242828 A1 | 12/2019 |
| WO | 2020008470 A1 | 1/2020 |
| WO | 2020010766 A1 | 1/2020 |
| WO | 2020014305 A1 | 1/2020 |
| WO | 2020016471 A1 | 1/2020 |
| WO | 2020035121 A1 | 2/2020 |
| WO | 2020044081 A1 | 3/2020 |
| WO | 2020055998 A1 | 3/2020 |
| WO | 2020076607 A1 | 4/2020 |
| WO | 2020076609 A1 | 4/2020 |
| WO | 2020084282 A1 | 4/2020 |
| WO | 2020125906 A1 | 6/2020 |
| WO | 2020125907 A1 | 6/2020 |
| WO | 2020128456 A1 | 6/2020 |
| WO | 2020128457 A1 | 6/2020 |
| WO | 2020156624 A1 | 8/2020 |
| WO | 2020156625 A1 | 8/2020 |
| WO | 2020156626 A1 | 8/2020 |

* cited by examiner

OSTOMY POUCH WITH FILTERING SYSTEM

CROSS REFERENCE

This application is a Continuation of U.S. application Ser. No. 13/248,704, filed on Sep. 29, 2011, which claims the benefit of U.S. Provisional Application No. 61/388,331, filed Sep. 30, 2010, both of which are incorporated herein by reference in their entireties.

FIELD OF THE INVENTION

The present invention relates to ostomy appliances and more particularly to ostomy pouches having a filter.

BACKGROUND OF THE INVENTION

Gas management and odor removal is of very significant concern in ostomy appliances. Despite the advances in various filter designs, there is still a need by ostomates for improved filter performance. Most ostomy filters currently on the market only work for a short time, in many instances less than 1 day. The key complaints have been leakage, clogging which leads to ballooning, insufficient deodorization, and reduced wear time. When some marketed filters stop working there can be leakage of stool outside of the pouch from the filter. Most of filter designs now utilize an oleophobic membrane to protect the filter from leaking in the presence of the enzymes and chemicals from feces. However, commercial ostomy pouches with or without oleophobic membranes have not addressed the clogging issue as effectively as desired by many ostomates. There are also ostomy pouches utilizing multiple membranes to improve both oleophobic and hydrophobic property in the filter, but this design increases the resistance of air flow significantly.

Most commercial ostomy filters are based on radial flow in which the gases flow along the plane of a relatively flat filter rather than directly or axially through the thickness of the filter. Such a radial or planar flow type is used in order to increase the reaction time between gases and the activated carbon. An axial flow type filter is difficult to make because of the difficulties involved in balancing the deodorization efficiency, the air flow requirement, and the profile of the filter. It is, however, desirable to have an axial flow filter that would allow a relatively small filter to be used without sacrificing the deodorization performance. A small filter size is preferred because it allows the filter to be positioned as close as possible to the seam of a pouch so that the face of the filter is not directly in front of the opening of the stoma, thus decreasing the tendency of filter clogging.

Accordingly, there is a need for an improved filtering system to improve clogging resistance. Furthermore, there is a need for an axial flow filter in order to minimize the filter profile and to make a small size filter possible.

SUMMARY OF THE INVENTION

One aspect of the invention in the filter design of the present invention is to improve the clogging resistance by using the newly developed pleated center panel design. This design includes a filter in the front panel of the pouch and a center panel of film that is intended to shield the filter from direct exposure to stool that is expelled from the stoma. The center panel has at least one pleat, and preferably two pleats, that are intentionally formed into the center panel. These pleats allow the gas to travel from the stoma area into the filter area while preventing a majority of the stool from get to and fouling the filter. Without these pleats the center panel has a tendency to block or seal against the front panel of the pouch and not allow gas to get to the filter and thus cause ballooning of the pouch. Optionally, an open cell foam can be added between the face of the filter and the pleats to further reduce any stool that might get past the pleats.

Another aspect of the invention is the incorporation of a filter designed for axial air flow. The pleated design makes possible the use of a small size filter which has a low profile. Both the strip filter and axially flow filter can be combined with the pleated center panel design to improve the clogging resistance.

Another aspect of the invention is a strip filter design, in which the filter is wrapped with an odor barrier film around its perimeter. Such a design allows the filter to maximize its deodorization performance without significantly increasing the air flow resistance.

A test method was devised to mimic actual usage of filtered pouches and their resistance to clogging. Testing was conducted on a specifically designed tilting table test rig. The test rig was designed to hold the test filtered pouches in the vertical position and tilt them to the horizontal position at timed intervals. The tilt table test rig also incorporates a means to inject air into the filtered test pouch to simulate gas produced by the body. The test pouches with filters are also filled with a simulated stool referred to as Feclone, which is commercially sold and mixed to a desired viscosity of 1 part solid to 3 parts water, to challenge the filtering system from a clogging perspective. When the testing is conducted, the filtering system is exposed to the simulated stool and simulated gas at timed intervals of 10 minutes in each position. Pouches are continuously cycled through the vertical and horizontal positions during this tilt table test. During each cycle the test pouches are injected with about 300 cc air to fill each pouch every 10 minutes with a fill time of 5 seconds. When the filter is not clogged, the test pouch deflates normally by releasing the air through the filter system. Testing is continued until all pouches have failed to release air from inside of the pouch, as indicated by the ballooning in the pouch. The criteria for filter failure is when a test filtered pouch fails to deflate and stays fully ballooned for 3 consecutive tilt table cycles. When ballooning occurs, the simulated stool clogs the filter and the filter system can no longer release the air.

Numerous commercial filtering systems were evaluated. Results of various pouch designs, with and without pleats, are summarized in FIG. 1. Testing showed that the center pleated panel filtering system doubled the life of the filter to around 300 minutes, which is defined by the time that the filter becomes clogged. Testing also showed that the pleated center panel filtering system when used with the foam tripled the life of the filter to around 600 minutes. Results of various pouch designs, with and without pleats, are summarized in FIG. 1. Clogging resistance was also compared with and without the foam in the filter system.

The physical dimension of an axial flow filter versus a radial flow filter is shown in Table 1. Table 2 is a summary of the $H_2S$ deodorization results of the same axial flow filter and the radial flow filter at various relative humidity and with different carrier gases. FIG. 2 is a graph of the results from Table 2. As can be shown from Table 2 and FIG. 2, an axially flow filter outperformed the radial flow filter in the $H_2S$ deodorization even though the activated carbon layer is thinner and the surface area is smaller.

TABLE 1

Physical Dimension of an Axial Flow
Filter versus a Radial Flow Filter

| | Radial Flow Filter (Freudenberg Improved Option 20 w/o ePTFE membrane), activated carbon thickness | Axial Flow Filter (Donaldson Nicom 39 with an ePTFE membrane) |
|---|---|---|
| Activated Carbon thickness, mm | 2.2 mm | 1.1 mm |
| Activated Carbon surface area, mm² | 484 | 270 |

TABLE 2

$H_2S$ Deodorization Breakthrough Time and Back Pressure

| | Radial Flow Filter (Freudenberg Improved Option 20 w/o ePTFE membrane), activated carbon thickness | | Axial Flow Filter (Donaldson Nicom 39 with an ePTFE membrane) | |
|---|---|---|---|---|
| % RH and Carrier Gas | $H_2S$ Deodorization Time, minutes | Back Pressure, mbar | $H_2S$ Deodorization Time, minutes | Back Pressure, mbar |
| 0%/$CH_4$ and N2 | 120-150 | −1 | 25-50 | −10 |
| 0%/Air | 40 | −1 | N/A | −10 |
| 5-7%/Air, | 170 @ 7% RH | −1 | 552 © 5% RH | −10 |
| 35%/Air, | 580 | −1 | 1500-2790 | −10 |
| 35%/$CH_4$ and $N_2$ | 320-483 | −1 | 270 | −10 |
| 35%/Air | 700-880 | −1 | 2353 | −10 |
| 50%/Air | 960-1240 | −1 | 3090 | −10 |
| 80%/Air | 1960 | −1 | 3940 | −10 |

Table 3 is a summary of the $H_2S$ deodorization results of a strip filter, in a rectangular dimension 15 mm×33 mm, versus a round filter with a diameter of 25.4 mm. Although the total surface area and the activated carbon thickness are about the same, the strip filter had significantly higher deodorization time due to the increased effective flow distance. In this example, the effective flow distance is almost 33% longer, resulting in a longer $H_2S$ deodorization time.

TABLE 3

$H_2S$ Deodorization of a Strip Filter versus a Round Filter

| | Strip Filter (Freudenberg Improved Option 20) | Round Filter (Freudenberg Improved Option 20) |
|---|---|---|
| Activated Carbon thickness, mm | 2.2 mm | 2.2 mm |
| Activated Carbon surface area, mm2 | 495 | 484 |
| Effective Flow Distance | 16 mm | 12 mm |
| H2S Deodorization Time, minutes (0%/$CH_4$ and $N_2$) | 138 | 108 |
| Back Pressure, mbar | 3.1 | 1.0 |

The present invention includes the following:

1. Pleated center panel that improves clogging resistance. An open cell foam can be added to further increase clogging resistance. This pleated design, with and without the foam, can be used with all types of filters, round or strip, radial flow or axial flow. The pleated design, with and without the foam, can be used in either drainable or closed pouch.

2. An axial flow filter with an equivalent or better deodorization time although the activated carbon layer is thinner and the surface area is smaller in an axial flow filter.

3. A strip filter with an equivalent or better deodorization time as a result of the increased effective flow distance, as compared to a round filter which has the about the same thickness and surface area.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE DRAWINGS

Figure 1:
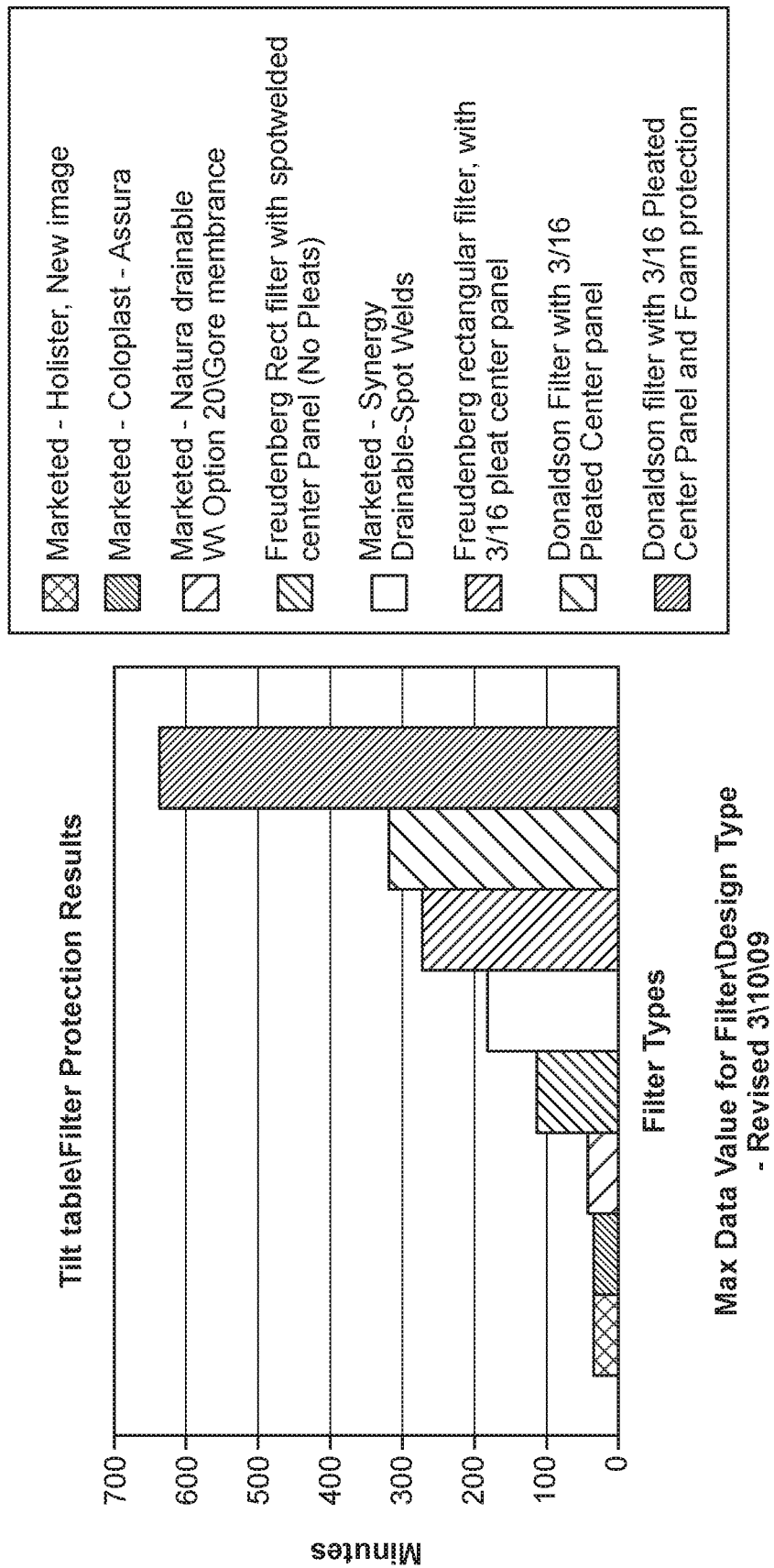
FIG. 1 is a graph of the life of filter defined by time to clog as tested by tilt table.
Figure 2:
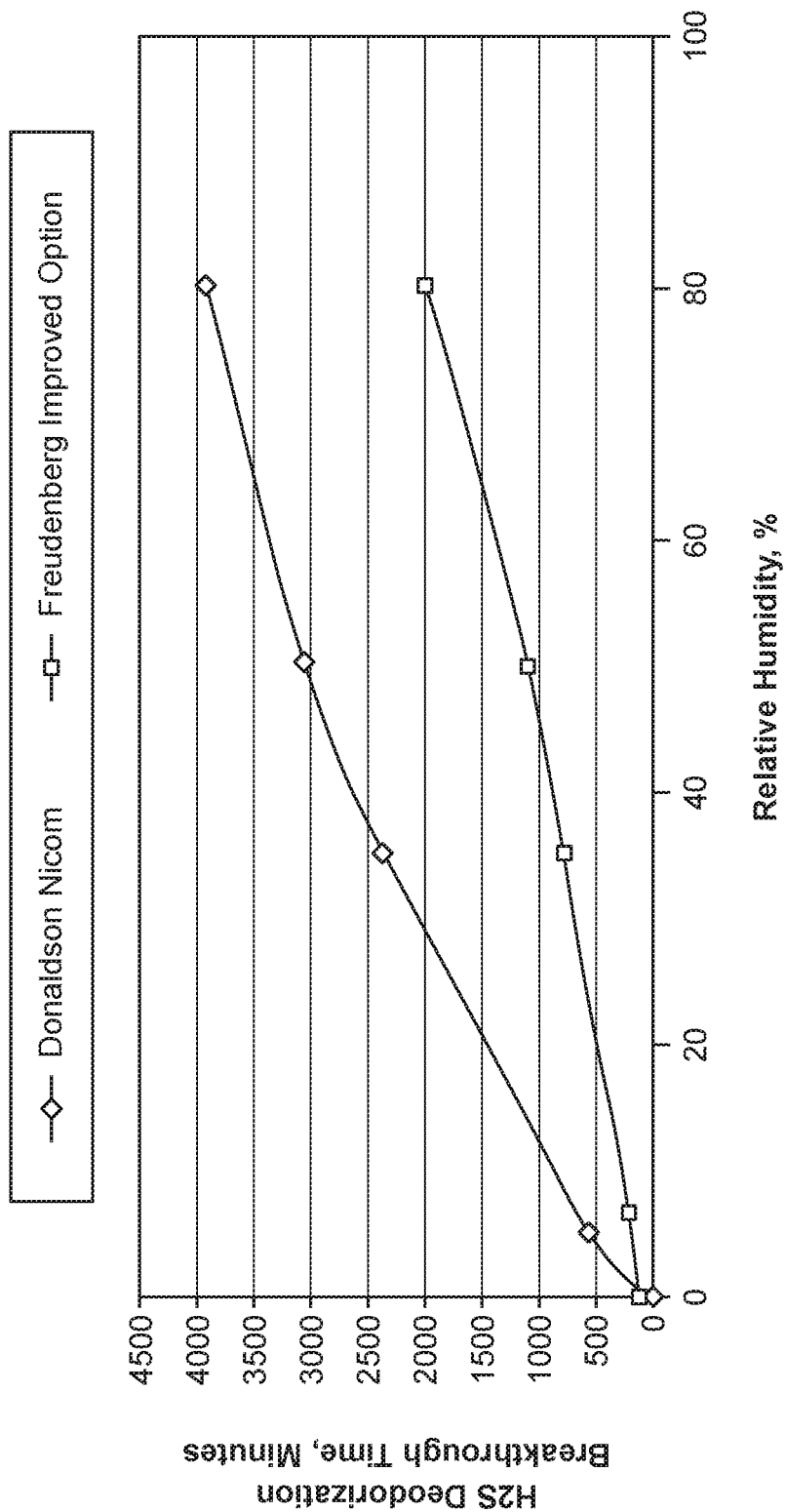
FIG. 2 is a graph of the effect of relative humidity on $H_2S$ deodorization breakthrough time in air.
Figure 3:
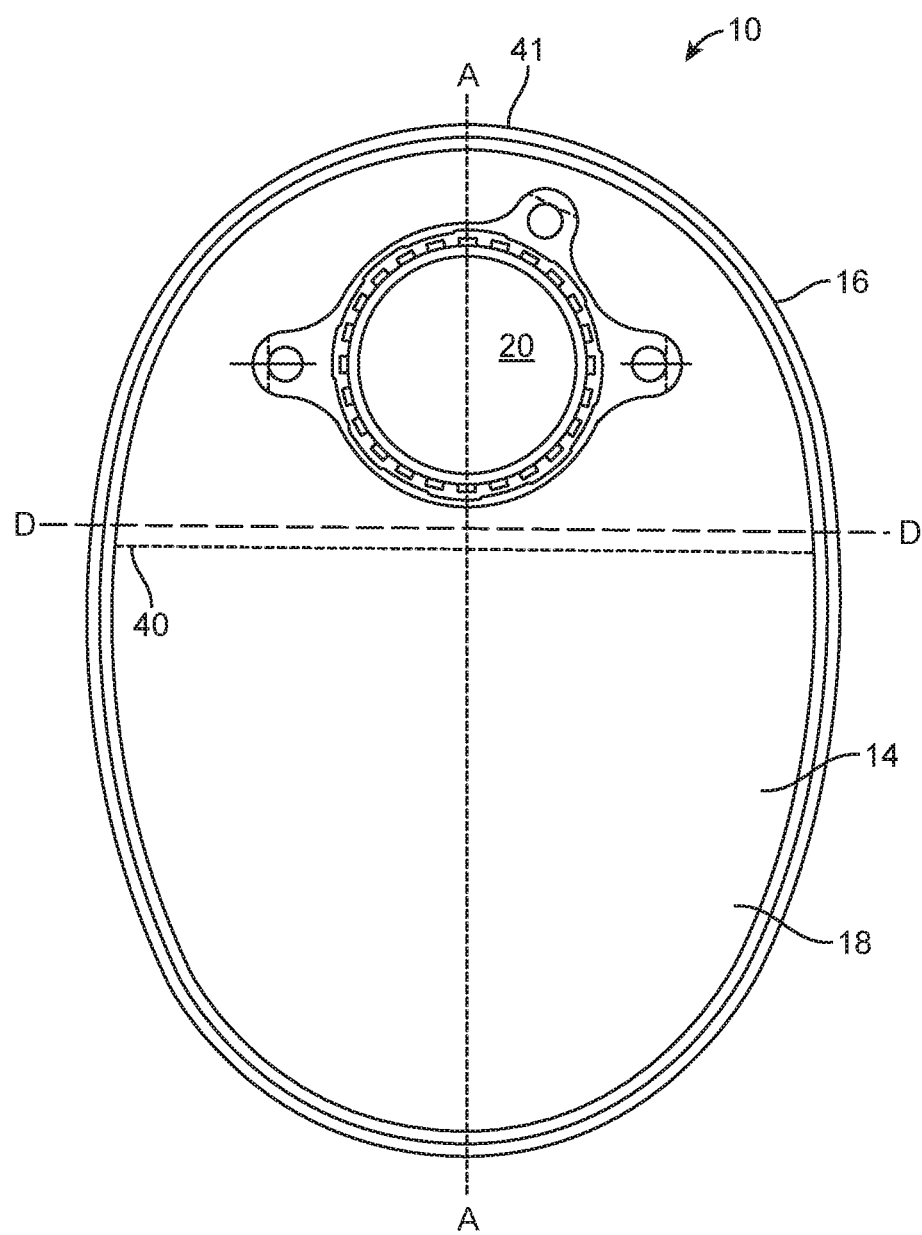
FIG. 3 is a rear elevational view of an ostomy appliance in accordance with the present invention.
Figure 4:
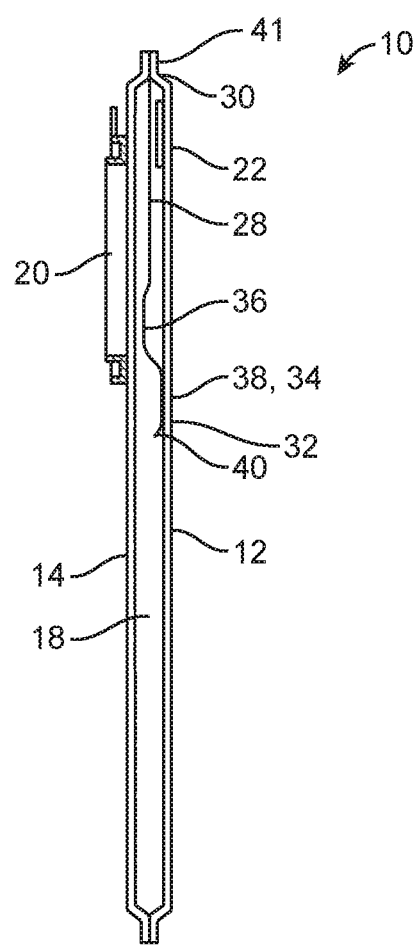
FIG. 4 is a cross-sectional view along line A-A of FIG. 1.
Figure 5:
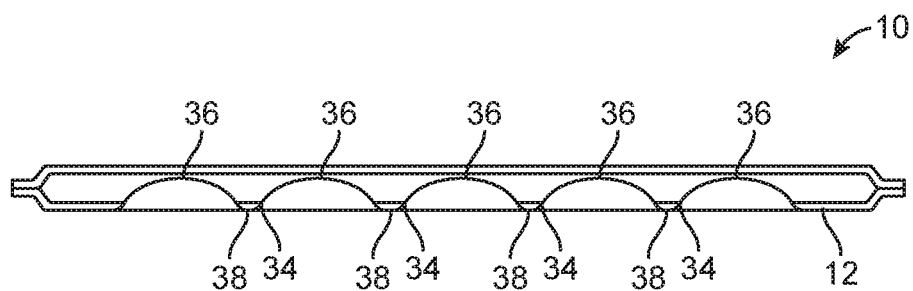
FIG. 5 is a cross-sectional view along line D-D of FIG. 1 (without the stomal flange and filter, for clarity).
Figure 6:
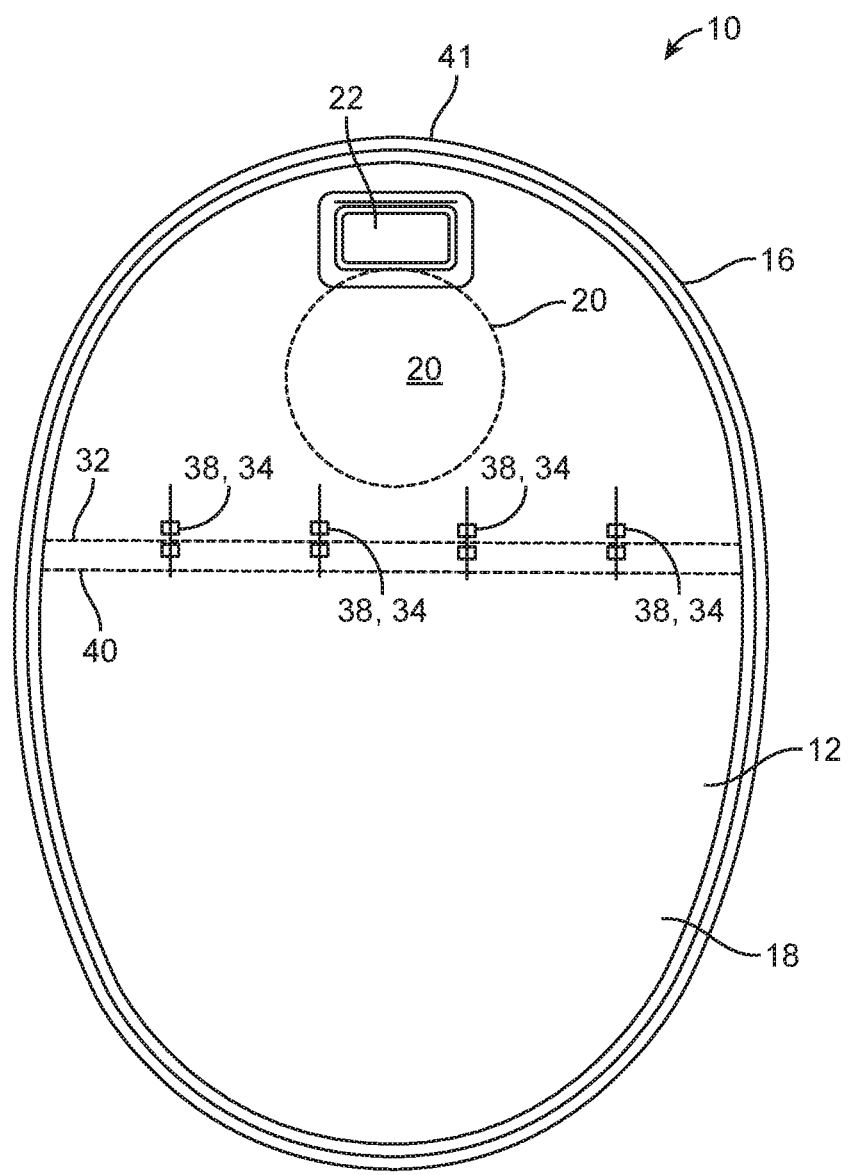
FIG. 6 is a front elevational view of the ostomy appliance of FIG. 1 (without the stomal flange, for clarity).

The present invention is an ostomy appliance 10 (FIGS. 3-6) having a front panel 12 and rear panel 14 that are sealed together around the peripheries of the panels to form the outer edge 16 of a closed ostomy pouch 18. The rear panel 14 includes a stomal opening 20 through which body waste is excreted when the ostomy pouch is appropriately placed on a body with the stomal opening 20 surrounding the stoma. The ostomy pouch 18 includes a filter assembly 22 attached to the front panel 12 typically by welding. The rear panel 14 includes an opening for permitting and facilitating the passage of the body waste odor deodorized by the filter assembly 22 to the atmosphere.

The ostomy pouch 18 further includes a center pleated panel 28 present between the front panel 12 and rear panel 14. This center pleated panel 28 includes an edge 30 attached to the outer edge 16 of the ostomy pouch 18. The center pleated panel has a partially free edge portion 32 that is attached intermittently 34 to the inner surface of the front panel 12. This center pleated panel 28 is predeterminedly dimensioned and attached to the front panel 12 in a manner to produce extra material in the form of folds, corrugations or pleats 36 within the pouch 18; the pleats 36 permit odorous gas to reach the filter assembly 22 for deodorization while deterring a ballooning of the pouch 18 due to captured gas within the pouch.

The pleated center panel 28 extends partially down from the top 36 of the ostomy pouch so as to at least partially and preferably totally cover and protect the filter assembly 22 from any body waste material entering the pouch 18 through the stomal opening 20. The pleats 36 are formed in part by the spot welds 38 securing the edge portion 32 to the front panel 12. The pleated center panel 28 has a bottom edge 40. The pleated center panel 28 is preferably made of the same standard ostomy pouch material used for the front panel 12 and rear panel 14.

Variations and modifications to the preferred embodiment may be made while falling within the scope of the invention, as defined by the claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. An ostomy appliance comprising a pouch comprising:
   a) a front panel comprising a filter assembly;
   b) a rear panel comprising a stomal opening for fitting around a stoma, wherein the front panel and rear panel are at least partly sealed to each other along their peripheries; and
   c) a center panel between the front panel and the rear panel comprising a top edge and a bottom edge, the center panel attached to the front and rear panel to at least partially cover the filter assembly to protect the filter assembly from coming into contact with bodily waste from the stomal opening, wherein the center panel is predeterminedly dimensioned and intermittently attached to the front panel to produce extra material, the extra material deterring ballooning of the pouch.

2. The ostomy appliance of claim 1, wherein the center panel is intermittently attached to a portion of the front panel by welds.

3. The ostomy appliance of claim 1, wherein the rear panel comprises an opening for permitting and facilitating passage of body waste odor deodorized by the filter assembly to the atmosphere.

4. The ostomy appliance of claim 1, further comprising an open cell foam positioned between the filter assembly and the center panel.

5. The ostomy appliance of claim 1, wherein the filter assembly is an axial flow filter or strip filter.

6. The ostomy appliance of claim 1, wherein the filter assembly is a strip filter.

7. The ostomy appliance of claim 6, wherein the strip filter is wrapped with an odor barrier film around its perimeter.

8. The ostomy appliance of claim 5, wherein the filter comprises activated carbon.

9. The ostomy appliance of claim 1, wherein the pouch is a drainable pouch.

10. The ostomy appliance of claim 1, wherein the pouch is a closed pouch.

* * * * *